(12) United States Patent
Lucas

(10) Patent No.: US 9,173,769 B2
(45) Date of Patent: Nov. 3, 2015

(54) POTENTIALLY REVERSIBLE FEMALE STERILIZATION DEVICE

(75) Inventor: Vincent Lucas, Lisieux (FR)

(73) Assignee: ASPIDE MEDICAL, La Talaudiere (FR)

( * ) Notice: Subject to any disclaimer, the term of this patent is extended or adjusted under 35 U.S.C. 154(b) by 401 days.

(21) Appl. No.: 13/805,849

(22) PCT Filed: Jun. 29, 2011

(86) PCT No.: PCT/FR2011/051512
§ 371 (c)(1),
(2), (4) Date: Jan. 31, 2013

(87) PCT Pub. No.: WO2012/001301
PCT Pub. Date: Jan. 5, 2012

(65) Prior Publication Data
US 2013/0160773 A1    Jun. 27, 2013

(30) Foreign Application Priority Data
Jul. 1, 2010  (FR) .................................... 10 55314

(51) Int. Cl.
*A61F 6/22* (2006.01)
*A61F 6/20* (2006.01)
*A61F 6/24* (2006.01)

(52) U.S. Cl.
CPC . *A61F 6/225* (2013.01); *A61F 6/20* (2013.01); *A61F 6/24* (2013.01)

(58) Field of Classification Search
CPC ...................................................... A61F 6/20
USPC ............. 128/842, 843, 830, 831; 604/385.17, 604/385.18, 904, 11, 385.04; 606/1, 606/191–193
See application file for complete search history.

(56) References Cited

U.S. PATENT DOCUMENTS 3,811,423 A * 5/1974 Dickinson et al. ............... 600/33
5,979,446 A   11/1999 Loy
(Continued)

FOREIGN PATENT DOCUMENTS

EP        0010812 A1    5/1980
WO    2004/021864 A2    3/2004
WO    2004/098469 A1   11/2004

OTHER PUBLICATIONS

International Search Report for International Application No. PCT/FR2011/051512, dated Aug. 31, 2011.

*Primary Examiner* — Victoria J Hicks
*Assistant Examiner* — Tarla Patel
(74) *Attorney, Agent, or Firm* — Heslin Rothenberg Farley & Mesiti P.C.

(57)   ABSTRACT

A reversible leave in contraceptive device includes an obturator having a body with cylindrical configuration, made of a flexible material and including two stabilizing deformable stiffeners that can be folded back along the obtorator body when unactivated, spreading out radially in a fitted situation in the isthmic part of the Fallopian tube. The stiffeners are in opposite positions so as to fit on one side in the isthmic part of the tube (for the distal side) and, on the other (proximal end) on edges of a tubal ostium. A plurality of projecting forms, having a ridged configuration, run along the entire length of the obturator body in a continuous manner from a tapered bulge of the proximal end to a spherical distal end of the head, and block the tubal protect tubal haustrations. The forms cause deformation of the alveoli to block spermatozoa and close off other mucosal folds.

12 Claims, 3 Drawing Sheets

(56) References Cited

U.S. PATENT DOCUMENTS

| | | | |
|---|---|---|---|
| 6,371,118 B1* | 4/2002 | Ray et al. | 128/830 |
| 2007/0227544 A1* | 10/2007 | Swann et al. | 128/831 |
| 2008/0154256 A1* | 6/2008 | Payne et al. | 606/34 |
| 2009/0056722 A1 | 3/2009 | Swann | |
| 2010/0006105 A1* | 1/2010 | Carter et al. | 128/831 |

* cited by examiner

POTENTIALLY REVERSIBLE FEMALE STERILIZATION DEVICE

CROSS REFERENCE TO RELATED APPLICATIONS

This application is a national stage filing under section 371 of International Application No. PCT/FR2011/051512, filed on Jun. 29, 2011, and published in French on Jan. 5, 2012, as WO 2012/001301 and claims priority of French application No. 1055314 filed on Jul. 1, 2010, the entire disclosure of these applications being hereby incorporated herein by reference.

BACKGROUND ART

The invention relates to the technical sector of female contraceptive means and methods.

Various methods of female contraception are known using oestroprogestative pills, progestin-only pills, hormonal intrauterine devices (IUD), copper IUDs, etc., and all these means and methods have well-known benefits and side effects. The use of male or female condoms is also common, as is pre-ejaculatory withdrawal, or certain natural methods (called symptom-based methods), the rhythm method or the cervical mucous method (Billings ovulation method). Sterilisation for contraceptive purposes is also performed, requiring the patient's free choice after consultation with a physician; some of these methods are performed abdominally and require general anaesthesia (either by laparotomy, laparoscopy or posterior vaginal culdotomy). Other methods have been tested hysteroscopically (uterine endoscopy) with the insertion of a cone plug, polyethylene plugs with spicules, or hydrogel-based plugs.

Currently, the reference method is the "Essure" device, which produces an inflammatory reaction. There is a risk that insertion may fail, while another disadvantage is that the technique is irreversible. It is an alternative to surgical sterilisation and consists in the selective occlusion of the Fallopian tube by inserting a micro-coil approximately 4 cm in length into each of the patient's Fallopian tubes. This micro-coil contains polyethylene terephthalate fibres that elicit a natural tissue reaction, which leads to occlusion.

From the prior art, we know of the reversible female sterilisation devices described in patents EP 0010812 and U.S. 2009/056722, which make it possible to obtain opposite forms on either side of a median tubal part that can be anchored into the Fallopian tube and its opening. More particularly, in the aforementioned US patent, the device has wing shapes with a conical configuration for anchoring in the aforementioned Fallopian tube. These devices are not, however, suited to the control of cell tissue deterioration inside the Fallopian tube.

We also know from U.S. Pat. No. 5,979,446 that there is a contraceptive device with flexible fingerlike protrusions around the sides and which is attached by anchoring it into the tubal mucosa, providing no protection and allowing spermatozoa to pass through.

The applicants have sought to remedy these drawbacks.

Their approach led to the need for a detailed examination of the Fallopian tube and a definition of its constituent characteristics. FIG. 1 is therefore provided to help to understand the invention, with the anatomy of the Fallopian tube comprising four successive parts starting from the uterus, i.e. a uterine or interstitial part (a), the median part (b) called the isthmic portion, the part comprising the ampulla/infundibulum (c), and the abdominal ostium. The first two parts, which are of interest for the invention, are 1 to 1.5 cm and 3 to 4 cm long, respectively. For the uterine or interstitial part, the ostial diameter is approximately 1 mm and the internal diameter, or lumen, is 0.2 to 0.5 mm. The diameter of an oocyte is 0.1 mm. For the isthmic portion, the lumen is 2 to 4 mm; it is cylindrical and its muscular wall is thick, hard and not very extensible.

Additionally, FIGS. 2, 2a, 2b and 2c represent the anatomy of the Fallopian tube to help to understand the invention. Sections A, B and C show the different sections corresponding to different areas of the Fallopian tube and present its internal structure. The number 1 indicates the peritoneum, 2 the subserosa, 3 the plexiform molecular layer, 4 the annular molecular layer, 5 the vessels, 6 the migration channel for ova and spermatozoa. Number 7 represents the alveoli formed randomly between the haustrations or mucous folds (8) inside the Fallopian tube.

In view of the aforementioned known prior art, and of the composition of the Fallopian tube, the Applicants' approach was to study a new design for female contraception that is natural, reversible and without undesirable side effects, and limiting cell destruction when removing the sterilisation device.

Given the problems posed, this analysis thus made it possible to develop a new, original solution for a new contraceptive method that is easy to implement while avoiding all inflammatory reactions and is reversible, in other words the initial situation can be returned to without any damage for the patient who desires another pregnancy.

BRIEF SUMMARY OF INVENTION

According to a first embodiment of the invention, the contraceptive device of the type comprising an obturator having a body with cylindrical or similar configuration, made of a flexible material and including two stabilisation means in the form of deformable stiffeners or wings that can be folded back along the body of the obturator when it is unactivated, spreading out radially in the fitted situation in the isthmic part of the Fallopian tube, the said means being in opposite positions so as to fit on one side in the isthmic part of the tube (for the distal side) and, on the other (proximal end) on the edges of the tubal ostium, is characterised in that the device comprises along its body a plurality of projecting forms, having a ridged configuration, running along the entire length of said obturator body in a continuous manner from the tapered bulge of the proximal end to the spherical distal end of the head and having a dual function on the one hand of blocking the tubal lumen and on the other of protecting the tubal haustrations, the said forms accommodating themselves within the alveoli formed in the body of the tube and being in contact with some of the mucosal folds or haustrations, causing the deformation of the alveoli to fulfill a dual function, on the one hand to block and obstruct the spermatozoa and on the other to close off the other mucosal folds in order to protect their surface and ensure the protection of the other closed mucosal folds not in direct contact, with a view to the reversibility of the contraceptive device.

Furthermore, and in a known manner, a protective sheath (playing the role of an applicator) surrounds the obturator and is entered into the isthmic part of the Fallopian tube and is then removed to deploy and anchor the stiffener or wing forms in the zone in question.

These characteristics and others will become clear in the rest of this description.

BRIEF DESCRIPTION OF THE DRAWING FIGURES

The subject of the invention is defined, as illustrated in a non-restrictive manner in the figures of the drawings, in which.

DETAILED DESCRIPTION

Figure 1:
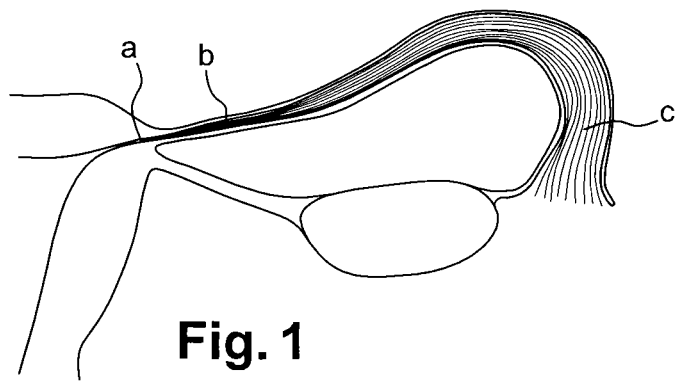
FIG. 1 is a representation of the internal structure of the Fallopian tube.
Figure 2A:
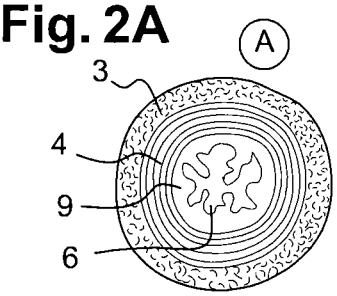
FIGS. 2, 2A, 2B and 2C are schematic views illustrating the anatomy of the Fallopian tube, according to various sectional positions.
Figure 2B:
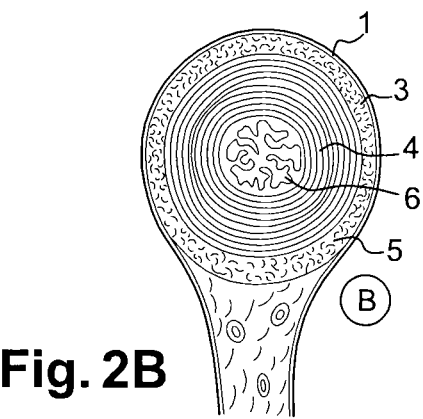
Figure 2C:
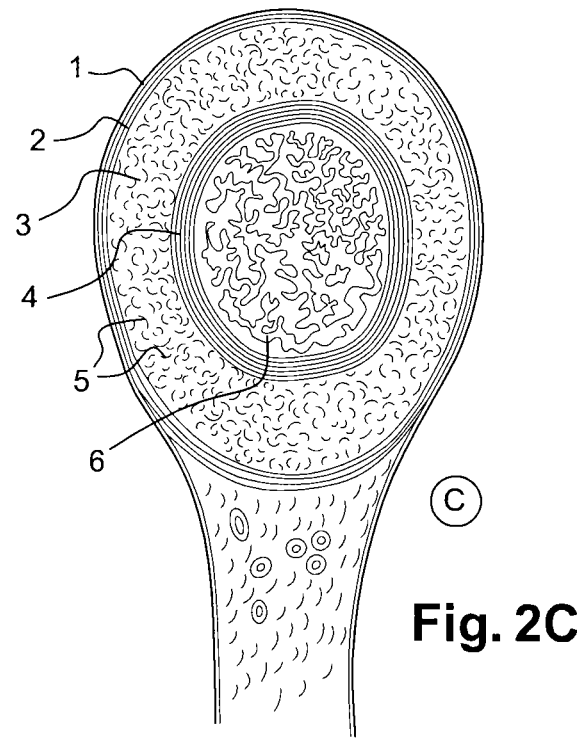
Figure 2:
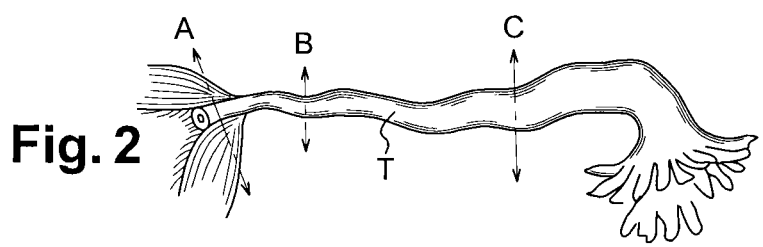

For a more concrete understanding of the subject of the invention, it will now be described in a non-restrictive manner as illustrated in the figures in the drawings.

Figure 9:
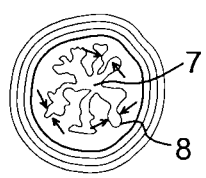
FIGS. 9 and 10 are schematic views providing a before-and-after illustration of the device's positioning in the Fallopian tube, notably in relation to its positioning with the mucosal folds and internal alveoli, with the dual function on the one hand of blocking the tubal lumen and on the other of protecting the tubal haustrations or mucosal folds.
Figure 10:
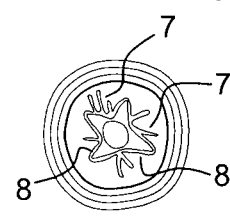
Figure 3:
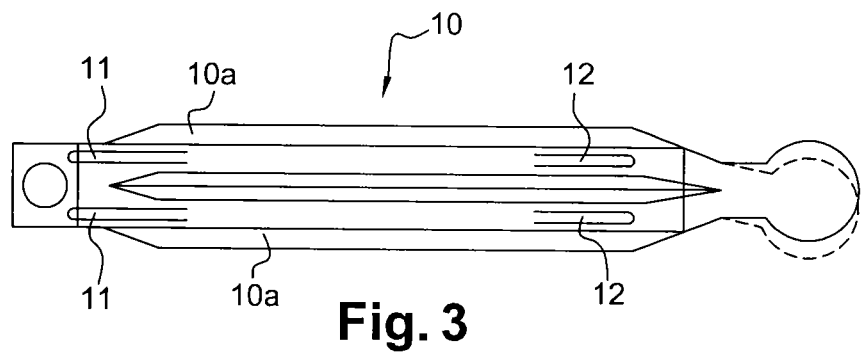
FIG. 3 is a schematic view illustrating the device according to the invention, with the longitudinal projections.
Figure 4:
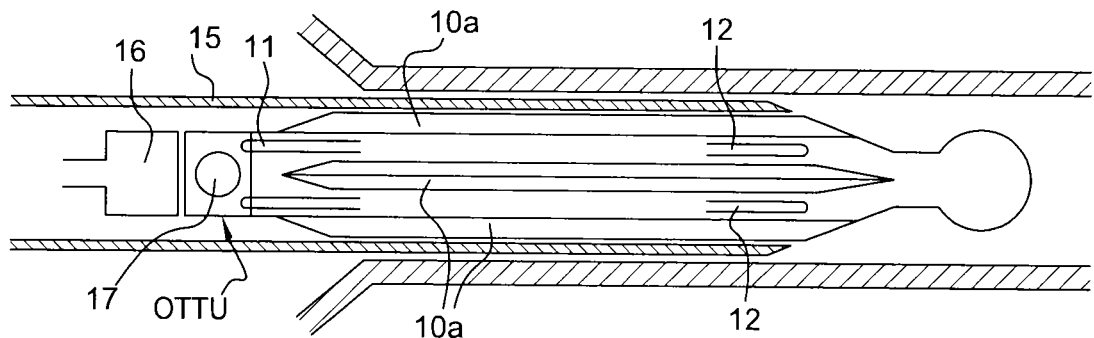
FIG. 4 is a schematic view illustrating the device inside an applicator and pre-positioned in the Fallopian tube.

The contraceptive device according to the invention is referenced as a whole by (10) and is designed to be inserted into the isthmic part of the Fallopian tube (T). It has the form of a cylindrical obturator with a plurality of projecting forms extending outward along its length (10a) and whose function is to obstruct the tubal lumen and to protect the tubal mucosa, in connection with the mucosal folds (8), filling all or part of the inside volume of the Fallopian tube defined by the alveoli. Some of the random mucosal folds come into contact with the walls of the projecting forms, causing a deformation of the alveoli to obstruct the passage of the spermatozoa. This contact can lead to an irreversible aspect of the sterilisation. The other alveoli are closed (FIG. 9) and protected without coming into direct contact with the implant, providing the desired reversible aspect after withdrawal of the device. Thus, said forms (10a) adapt inside the alveoli (7) formed in the body of the Fallopian tube and come into contact with some of the mucosal folds or haustrations (8), producing the deformation of the alveoli (7) to perform a dual function, on the one hand to block and obstruct the spermatozoa and on the other to close off the other mucosal folds in order to protect their surface and ensure the protection of the other closed mucosal folds not in direct contact, with a view to the reversibility of the device. The reversible aspect is ensured after removal of the implant by cell migration from the protected haustrations toward those that were in direct contact with the implant. These protruding forms (10a) can be arranged regularly along the body of the obturator with identical spacing. In another embodiment, they can be different and irregularly spaced in relation to one another. These protruding forms may be of the same configuration and the same height. In another embodiment, these protruding forms may have an irregular configuration. As represented in FIG. 3, the head (10b) of the obturator may be an extension along the axis of its body or significantly offset for easier insertion of the device into the Fallopian tube.

This obturator is made of a flexible material such as silicone or another non-recolonisable material so as not to injure or damage the walls in the Fallopian tube environment where it is placed (or another atraumatic material that avoids a fibrosis tissue reaction to the implant). Near its distal and proximal ends, the obturator has two means (11-12) having a configuration with stiffeners laid out in opposite directions to each other.

These means (11-12) are arranged radially around the body of the obturator, producing deformable stiffener or wing forms that can be folded back along the body of the obturator when it is unactivated before being fitted into place. These stiffeners or wings can be produced with the body of the obturator in a single piece and therefore of the same material. The means (12) arranged near the distal end opens out into the ampullary region of the Fallopian tube so that it is anchored into the surrounding mucosa, and can be folded back or at least will not hinder the removal of the contraceptive device. The length of the stiffeners is sufficient to be anchored in the mucosa. The second anchoring means (11) is on the proximal end of the obturator. The projecting forms (10a) are arranged in a continuous manner along the entire body of the obturator from the tapered bulb on the proximal end to the distal end of the head 10(b). These projecting forms have a ridged configuration whose continuous base is the body of the obturator.

It should be pointed out that said proximal end has an opening (17) for inserting and running a cord or other means for withdrawing the device if pregnancy is desired. Before inserting the device into the isthmic part of the Fallopian tube, it is inserted into a sheath (15) which flattens the means (11-12) along the body of the obturator. Then, pushed by a plunger (16), the obturator device is released into the isthmic part of the Fallopian tube, withdrawing the sheath through a counterthrust effect, and the means (11-12) are deployed radially and are anchored.

The contraceptive device according to the invention is inserted visually using a hysteroscope.

Figure 5:
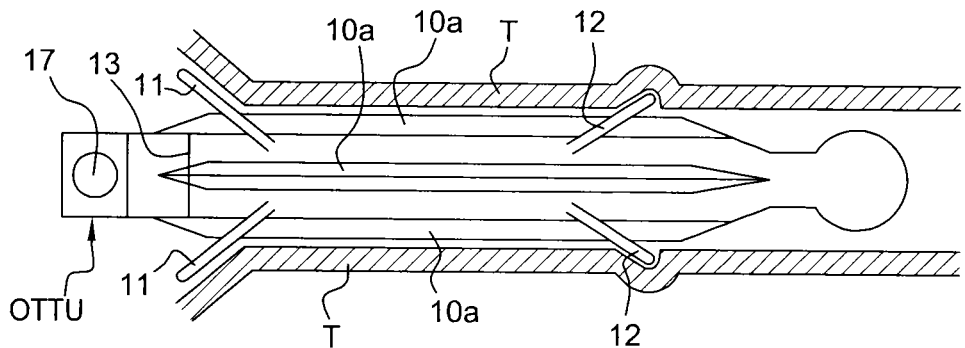
FIG. 5 is a view according to FIG. 4 after removal of the applicator.
Figure 6:
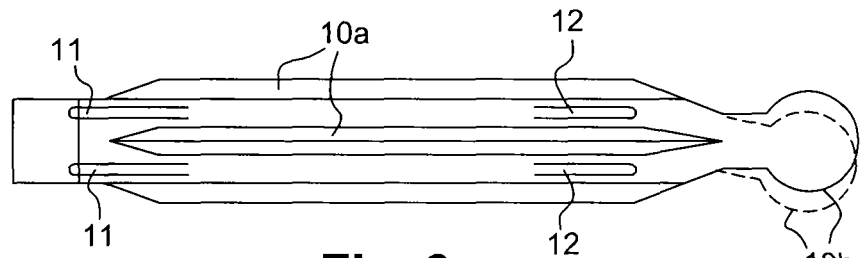
FIG. 6 is a view of a variation of the device with the head offset from the axis.
Figure 6A:
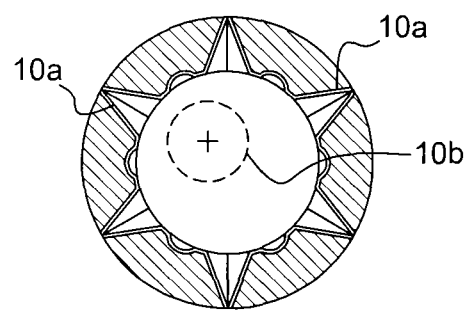
FIG. 6a is a frontal view and a sectional view according to FIG. 6.
Figure 7:
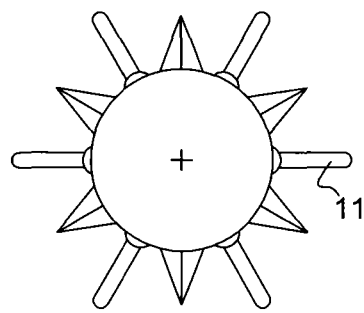
FIG. 7 is a sectional view of the obturator device according to the invention, notably illustrating the projecting forms along its body.
Figure 8:
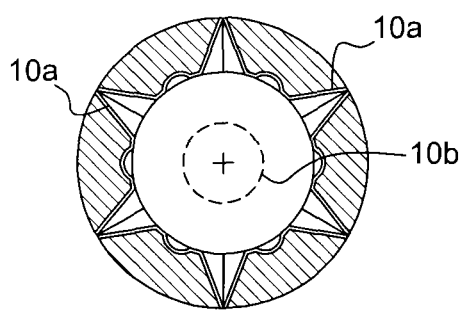
FIG. 8 is a view illustrating the device inserted (in the Fallopian tube) with the applicator in place.

A marker or locator means (13), FIG. 5, in any suitable material, designed to be identified and located by a reading means of the type used in ultrasonography and standard radiology is arranged on the device (10). Advantageously, it is located behind the first means (11).

The device also comprises a means of withdrawal (17) in the form of a reach-through opening arranged behind the anchoring means (11) and enabling said withdrawal.

The means (12) located at the distal end has stiffeners in the form of an umbrella smaller than the means (11) located at the proximal end.

The advantages of the contraceptive device according to the invention lie in the quality of the blockage provided by the body of the obturator, notably thanks to said protruding forms (10a) which ensures a perfect seal against the inside of the Fallopian tube. Furthermore, all the mucosal folds and all the alveoli are not systematically in contact of the obturator tube and its projecting forms (10a) which, in case of deterioration, allows migration and cell regeneration so as to restore the damaged alveoli after withdrawal of the device.

Furthermore, the design of the device according to the invention creates folds in the tubal mucosa, which is a source of protection for the mucosa and a source of repair for the folds that come into contact with the device.

Furthermore, there is no risk of inflammation of the walls of the Fallopian tube, which is essential. This contraceptive method is reversible as the obturator device can be withdrawn easily, with no resistance from the anchoring due to the orientation of the anchoring means (11) and the specificity of the forms (10*a*) inside the Fallopian tube.

The invention claimed is:

1. Contraceptive device comprising an obturator having a body with a cylindrical configuration, made of a flexible material and including two stabilizing deformable stiffeners or wings that can be folded back along the body of the obturator when unactivated, spreading out radially in a fitted situation in an isthmic part of a Fallopian tube, the two stabilizing deformable stiffeners or wings being in opposite positions so that a distal one of the two stabilizing deformable stiffeners or wings is situated to fit in the isthmic part of the Fallopian tube and a proximal one of the two stabilizing deformable stiffeners or wings is situated on edges of a tubal ostium, wherein the device further comprises, along the body, a plurality of projecting forms, having a ridged configuration, running along an entire length of said obturator body in a continuous manner from a tapered bulge of the proximal end to a spherical distal end of a head and having a dual function of blocking a tubal lumen and protecting tubal haustrations, the projecting forms accommodating themselves within alveoli formed in a body of the Fallopian tube and being in contact with some of mucosal folds or haustrations, causing deformation of the alveoli to block and obstruct spermatozoa and to close off other mucosal folds in order to protect their surface and ensure protection of other closed mucosal folds not in direct contact, the contraceptive function of the contraceptive device being reversible.

2. Device according to claim 1, wherein the obturator comprises a silicone-based material.

3. Device according to claim 1, wherein the projecting forms are identical.

4. Device according to claim 1, wherein the projecting forms are different.

5. Device according to claim 1, wherein the projecting forms are regularly spaced along the obturator body.

6. Device according to claim 1, wherein the projecting forms are irregularly spaced along the obturator body.

7. Device according to claim 1, wherein the two stabilizing deformable stiffeners or wings are oppositely directed.

8. Device according to claim 7, further comprising a marker to be identified and located by a reading means using ultrasonography.

9. Device according to claim 7, further comprising a reach-through opening arranged behind the proximal one of the two stabilizing deformable stiffeners or wings and enabling device withdrawal.

10. Apparatus for fitting and introducing the device according to claim 1, comprising a sheath ensuring positioning of the two stabilizing deformable stiffeners or wings along the obturator body before anchoring the device.

11. Apparatus for fitting and introducing the device according to claim 10, further comprising a plunger for positioning the device by pushing until the obturator device is released in the isthmic part of the Fallopian tube by withdrawing the sheath.

12. Device according to claim 1, wherein the obturator comprises a non-recolonizable material.

* * * * *